(12) United States Patent
Li et al.

(10) Patent No.: US 12,310,779 B2
(45) Date of Patent: May 27, 2025

(54) METHOD AND DEVICE OF CORRECTION OF RING ARTIFACT IN CT IMAGE AND COMPUTER PROGRAM MEDIUM

(71) Applicant: RAYCAN Technology Co., Ltd. (Suzhou), Suzhou Jiangsu (CN)

(72) Inventors: Ang Li, Suzhou Jiangsu (CN); Qingguo Xie, Suzhou Jiangsu (CN); Peng Xiao, Suzhou Jiangsu (CN)

(73) Assignee: RAYCAN Technology Co., Ltd. (Suzhou), Jiangsu (CN)

( * ) Notice: Subject to any disclaimer, the term of this patent is extended or adjusted under 35 U.S.C. 154(b) by 337 days.

(21) Appl. No.: 17/790,168

(22) PCT Filed: Sep. 3, 2020

(86) PCT No.: PCT/CN2020/113215
§ 371 (c)(1),
(2) Date: Jun. 30, 2022

(87) PCT Pub. No.: WO2021/135339
PCT Pub. Date: Jul. 8, 2021

(65) Prior Publication Data
US 2023/0088126 A1    Mar. 23, 2023

(30) Foreign Application Priority Data
Dec. 30, 2019    (CN) .................. 201911392508.X

(51) Int. Cl.
*A61B 6/00*    (2024.01)
*A61B 6/03*    (2006.01)
*A61B 6/42*    (2024.01)

(52) U.S. Cl.
CPC ............ *A61B 6/5258* (2013.01); *A61B 6/032* (2013.01); *A61B 6/4208* (2013.01); *A61B 6/5211* (2013.01)

(58) Field of Classification Search
None
See application file for complete search history.

(56) References Cited

U.S. PATENT DOCUMENTS

| | | | |
|---|---|---|---|
| 7,676,073 | B2 | 3/2010 | Hamill et al. |
| 2013/0101080 | A1 | 4/2013 | Moghe et al. |

FOREIGN PATENT DOCUMENTS

| | | |
|---|---|---|
| CN | 102451015 A | 5/2012 |
| CN | 102521801 A | 6/2012 |

(Continued)

OTHER PUBLICATIONS

Rashid et al. ("An improved method for the removal of ring artifacts in high resolution CT imaging", EURASIP Journal on Advances in Signal Processing 2012, 2012:93 http://asp.eurasipjournals.com/content/2012/1/93). (Year: 2012).*

(Continued)

*Primary Examiner* — Randolph I Chu
(74) *Attorney, Agent, or Firm* — Ohlandt, Greeley and Perle, L.L.P.

(57) ABSTRACT

Provided in the invention is a method and a device of Correction of a ring artifact in a CT image and a computer program medium. The method of correction comprises: pre-processing original detection data; marking a bad detector according to data in the pre-processed original sinogram; acquiring a replacing detection value corresponding to the bad detector by means of a first averaging processing; and performing a CT image reconstruction using a sinogram data after the first averaging processing. The device comprises: a pre-processing unit configured to pre-process original detection data; a marking unit configured to mark a bad detector according to data in the pre-processed original sinogram; a first averaging processing unit configured to acquire a replacing detection value corresponding to the bad detector by means of a first averaging processing; and an image (Continued)

reconstruction unit. The invention is able to effectively eliminate the ring artifact in the CT image, and at the same time ensure that there is little loss of the spatial resolution of the CT image.

30 Claims, 6 Drawing Sheets

(56) References Cited

FOREIGN PATENT DOCUMENTS

| CN | 108109185 A | 6/2018 | |
|---|---|---|---|
| CN | 109187591 A | 1/2019 | |
| CN | 109801343 A | 5/2019 | |
| CN | 110400358 A | 11/2019 | |
| CN | 111053568 A | 4/2020 | |
| CN | 112233030 B | * 1/2023 | ........... G06N 3/0454 |
| JP | 2010252951 A | 11/2010 | |

OTHER PUBLICATIONS

International Search Report dated Dec. 7, 2020 for PCT Appl. No. PCT/CN2020/113215.

Chinese Office Action dated Apr. 2, 2021 for Chinese Appl. No. CN 201911392508.X.

Suhong,Huang; "A Thesis Submitted to Chongqing University in Partial Fulfillment of the Requirement for the Degree of Master of Engineering"; College of Automation of Chongqing University; Apr. 2011; pp. 1-78.

* cited by examiner

METHOD AND DEVICE OF CORRECTION OF RING ARTIFACT IN CT IMAGE AND COMPUTER PROGRAM MEDIUM

The application claims the priority of Chinese patent application 201911392508.X filed on Dec. 30, 2019, the entire contents of which are incorporated herein by reference.

TECHNICAL FIELD

The invention relates to the field of CT image processing, more particularly to a method and a device of correction of a ring artifact in a CT image based on a sinogram, and a computer program medium.

BACKGROUND

CT is a conventional medical imaging apparatus, which generally comprises a scanning portion, a computer system, and an image display and storage system. The scanning portion comprises an X-ray tube, a detector module, a scanning frame and the like. The X-ray tube emits an X-ray beam to scan a scanned object and the detector module receives and converts the X-ray after passing through the scanned object into a visible light which in turn is converted into an electrical signal by means of photoelectric conversion. The computer system is responsible for the storage and operation of the electrical signal data collected through the scanning. The image display and storage system is responsible for displaying the images, which are processed and reconstructed by the computer system, through a TV screen, a multi-frame camera, or a laser camera. Specifically, as shown in FIG. 1, the scanning principle of the CT may be simply summarized as detecting the attenuation of the X-ray by the object in multiple angles. For example, for a cone-beam CT, when it scans, the X-ray emitted by the X-ray tube 1 irradiates the scanned object 3 placed between the X-ray tube 1 and the X-ray detector module 2 which typically comprises a plurality of sequentially arranged detectors 21 (FIG. 2). The detectors are arranged in rows or columns, and the detectors in each row or column may be referred to as one channel. The X-ray detector module 2 is able to detect the intensities of the X-ray in various positions after attenuation by the scanned object 3, and the intensities may be compared with the unattenuated intensity of the X-ray to calculate the attenuation coefficients. Subsequently, the X-ray tube 1 and the X-ray detector module 2 simultaneously are rotated 360° around the z-axis to accomplish a scanning. The attenuation coefficients acquired in the scanning in the various angles in the various positions may further form a projection map of each angle. The projection map may be represented in the form of a sinogram, as shown in FIG. 3, which is the form to express the CT original data. Each line of the sinogram represents the data sampled from one row of the channels of the detectors in one of the scanning angles of the detectors in the x direction (as shown in FIG. 1), and the data may be of X-ray intensities, attenuation coefficients, or the attenuation coefficients after a slope filtering. A two-dimensional matrix may be produced by arranging each line of the data in the angular sequence, and each element in the two-dimensional matrix may be represented by I(s, θ), where θ represents a scanning angle of a detector and the scanning angles are to take the irradiation direction of the X-ray when initiating the scan, or other known direction, as a reference, and s represents one of the positions in a row of the detectors. Since there are multiple rows of channels of detectors in the x direction and one sinogram may be acquired from each row of the channels by scanning the multiple angles, multiple sinograms may be acquired in one scanning.

When it cannot read out the signal normally or correctly from one of the channels, that is, when there is a damaged detector 21 or there is an abnormal response, the channel is referred to as a bad channel, as shown in the squares 22 with different gray values in FIG. 2. When the detector is damaged such that it cannot normally read out the signal, the gray value is relatively deep; when it cannot correctly read out the signal from the detector, the gray value is relatively shallow. Since the X-ray tube and the X-ray detector module are simultaneously rotate 360 degrees during the scanning of the CT, when there are some bad channels in the X-ray detector module or uneven responses in some channels (hereinafter collectively referred to as bad channels), there typically will be ring artifacts appeared in the reconstructed image, which will directly affect the quality of the CT image for the reader's review. Nevertheless, in practical uses, the cost will be too high to replace the detector module only if there are a small number of bad channels. Therefore, image correction methods are usually employed to eliminate the influence of bad channels.

At present, the methods of correction of a ring artifact in a CT image can be classified into image-based ring artifact correction, sinogram-based ring artifact correction, and deep learning-based ring artifact correction. Among them, the deep learning-based ring artifact correction method represents a favorable effect, but it requires a large number of medical images as training samples. However, the medical image samples are difficult to be acquired due to various reasons, leading to difficulty in the popularization and application of this method. For the other two correction methods, there is a tough dilemma: if a less loss of spatial resolution of the image were to be realized, the relatively light ring artifact will not be removed completely; and if the relatively light ring artifact were to be removed completely, there will be a greater loss of the spatial resolution of the image.

Therefore, it is necessary to develop a method of correction of a ring artifact in a CT image to overcome the above-mentioned technical problems.

SUMMARY

The objective of the invention is to provide a method and device of correction of a ring artifact in a CT image, and a computer program medium, thereby solving the problem in the prior art that the correction method has to be compromised between the quality of correction and the image spatial resolution.

In the invention provided is a method of correction of a ring artifact in a CT image, comprising:
  step S1: pre-processing original detection data;
  step S2: marking in detectors a bad detector based on the data in a pre-processed original sinogram;
  step S3: acquiring a replacing detection value corresponding to the bad detector by means of a first averaging processing; and
  step S4: performing a CT image reconstruction using a sinogram data after the first averaging processing.

According to an embodiment of the invention, the method of correction further comprises: prior to the step S1, establishing an additive noise model:

$$I(s,\theta)=I_r(s,\theta)+b(s)+\varepsilon(s,\theta),$$

wherein, I(s, θ) represents an actual detection value in a scanning angle θ in a detector position s in the original sinogram, and $I_r$(s, θ) represents an ideal detection value in the scanning angle θ and in the detector position s in an ideal sinogram; b(s) represents an offset value of the actual detection value corresponding to the detector position s, and ε(s, θ) represents a random error corresponding to the scanning angle θ and the detector position s in the original sinogram.

In an embodiment of the invention, in the step S1, the pre-processing comprises specific steps of:
  step S11: selecting actual detection values corresponding to a plurality of scanning angles θ from the original detection data to form the original sinogram;
  step S12: filtering the original sinogram in directions of detector positions s;
  step S13: acquiring a noise of the original sinogram by means of the filtering;
  step S14: performing a second averaging of the noise in directions of the scanning angles θ; and
  step S15: acquiring a standard deviation of the noise in the step S13 in the θ directions.

In an embodiment of the invention, in the step S11, the number of the selected scanning angles θ is not less than 50.

In an embodiment of the invention, in the step S11, the actual detection values are intensities of the X-ray after attenuation measured by the detector, attenuation coefficients thereof, or the attenuation coefficients after a slope filtering.

In an embodiment of the invention, in the step S12, the filtering is weighted filtering.

In an embodiment of the invention, in the step S12, the weighted filtering is mean filtering which employs the formula below:

$$I_r(s,\theta)=\Sigma_{-n}^{n} I(s+n,\theta)/(2n+1),$$

where n is a natural number.

In an embodiment of the invention, in the step S13, the noise is acquired by subtracting ideal detection values in an ideal sinogram after the filtering from the actual detection values in the original sinogram.

In an embodiment of the invention, in the step S14, the second averaging of the noise in the directions of the scanning angles θ may be specifically performed according to the following formula:

$$\hat{b}(s)=\Sigma_{\theta=1}^{N}[b(s)+\varepsilon(s,\theta)]/N,$$

wherein, $\hat{b}(s)$ represents an average offset value of offset values b(s) in the directions of all the scanning angles θ, and N is the number of the scanning angles θ selected in the step S11.

In an embodiment of the invention, in the step S15, the standard deviation of the noise in a detector position s is acquired according to the following formula:

$$\text{std}[\varepsilon(s)]=\Sigma_{\theta=1}^{N}[b(s)+\varepsilon(s,\theta)-\hat{b}(s)]^2/N,$$

wherein N is the number of the scanning angles θ selected in the step S11.

In an embodiment of the invention, in the step S2, marking the bad detector is performed by determining whether the following formula holds:

$$\text{abs}[\hat{b}(s)]>d\times\text{std}[\varepsilon(s)]\div\text{sqrt}(N) \qquad \text{(Formula 6)}$$

wherein, abs[$\hat{b}(s)$] represents an absolute value of the average offset value, d represents a correction coefficient, sqrt(N) represents a root mean square of N, and if the Formula (6) holds, it is determined that the average offset value $\hat{b}(s)$ is of excessiveness, and the corresponding channel is marked as the bad detector.

In an embodiment of the invention, the correction coefficient d is in a range of 1.6-2.6, 1.8-2.0 or 2.0-2.6.

In an embodiment of the invention, the correction coefficient d is 1.96.

In an embodiment of the invention, in the step S3, the first averaging processing comprises a specific step of: using an average value of the actual detection values of the 2n detectors adjacent to the bad detector on both sides thereof in the same line as the replacing detection value of the bad detector, wherein n is a natural number.

In an embodiment of the invention, in the step S3, where the CT detectors are arranged in a two-dimensional arrangement, the first averaging processing comprises a specific step of: using an average value of the actual detection values of the four detectors next to the bad detector as the replacing detection value of the bad detector.

In an embodiment of the invention, in the step S3, where the CT detectors are arranged in a two-dimensional arrangement, the first averaging processing comprises using an average value of the actual detection values of the eight detectors adjacent to the bad detector as the replacing detection value of the bad detector.

In an embodiment of the invention, in the step S3, where the CT detectors are arranged in a two-dimensional arrangement, the first averaging processing comprises a specific step of: using an average value of the actual detection values of the eight detectors in orthogonal directions to the bad detector as the replacing detection value of the bad detector.

In an embodiment of the invention, in the step S3, where the CT detectors are arranged in a two-dimensional arrangement, the first averaging processing comprises a specific step of: using an average value of the actual detection values of the twelve detectors adjacent to the bad detector as the replacing detection value of the bad detector.

In an embodiment of the invention, in the first averaging processing, the actual detection value of each detector is replaced by subtracting the corresponding average offset value from the actual detection value thereof.

In an embodiment of the invention, in the step S4, in the sinogram data, only the data at the bad detector is replaced by the replacing detection value, and the sinogram data at the non-bad detectors remain the same as the original sinogram.

In an embodiment of the invention, in the step S4, in the sinogram data, the data at the bad detector is replaced by the replacing detection value, and the sinogram data at the non-bad detectors are replaced by subtracting the average offset value from the original sinogram.

In the invention provided is a device of correction of a ring artifact in a CT image, comprising: a pre-processing unit configured to pre-process original detection data; a marking unit configured to mark a bad detector according to data in the pre-processed original sinogram; a first averaging processing unit configured to acquire a replacing detection value corresponding to the bad detector by means of a first averaging processing; and a reconstruction unit configured to perform a CT image reconstruction using a sinogram data after the first averaging processing.

In an embodiment of the invention, the pre-processing unit further comprises: a data acquisition subunit configured to select actual detection values corresponding to a plurality of scanning angles from the original detection data to form the original sinogram; a filtering subunit configured to filter the original sinogram in directions of the detector positions s; a noise acquisition subunit configured to acquire a noise of the original sinogram by means of the filtering; a second averaging subunit configured to perform a second averaging of the noise in directions of the scanning angles; and a standard deviation acquisition subunit configured to acquire a standard deviation of the noise in the directions of the scanning angles.

In an embodiment of the invention, the second averaging subunit is configured to output an offset value of the actual detection value after the second averaging.

In an embodiment of the invention, the first averaging processing uses an average value of the actual detection values of the 2n detectors adjacent to the bad detector on both sides thereof in the same line as the replacing detection value of the bad detector, n is a natural number.

In an embodiment of the invention, where the CT detectors are arranged in a two-dimensional arrangement, the first averaging processing uses an average value of the actual detection values of the four detectors next to the bad detector as the replacing detection value of the bad detector.

In an embodiment of the invention, where the CT detectors are arranged in a two-dimensional arrangement, the first averaging processing uses an average value of the actual detection values of the eight detectors adjacent to the bad detector as the replacing detection value of the bad detector.

In the invention, provided is a computer program medium in which program instructions are stored, and when executed, achieve the following functions: pre-processing an original sinogram; marking a bad detector in the pre-processed original sinogram; acquiring a replacing detection value corresponding to the bad detector by means of a first averaging processing; and performing a CT image reconstruction using the data after the first averaging processing.

In the invention, the obvious ring artifact in the image is usually generated by the bad channel, such that by analyzing the additive noise model, it may effectively detect the obvious bad channel using the method based on the hypothesis test in the statistical principle, and it may also eliminate the obvious ring artifact in the image by replacing the detection value of the bad detector with the average value of the detection values of the adjacent detectors. The ring artifact which is not particularly obvious in the image is usually caused by the inconsistency of the channel detection efficiency. The invention represents the effect of suppressing the ring artifact by subtracting the offset value of the channel to determine its detection efficiency. The invention only needs to replace the bad detector, which is in a small proportion, with the average value of the adjacent channels, so as to reduce the loss of the spatial resolution of the image to the greatest extent and ensure the quality of the image.

In a word, the method and device of correction of the ring artifact in the CT image and computer program medium provided in the present invention require no training before correction, are able to basically eliminate the ring artifact in the CT image, and at the same time ensure that there is little loss of the spatial resolution of the CT image, which has positive significance to the CT image correction and is facilitated to saving the cost.

BRIEF DESCRIPTION OF THE DRAWINGS

The accompanying drawings with reference to the embodiments or state of art will be described for the purpose of demonstrating the embodiments of the invention and the state of art. It is apparent that the figures as shown are merely illustrative of some embodiments as recited in the disclosure. It should be understood by those skilled in the art that various alternatives to the figures as shown may be appreciated, without creative work involved.

DETAILED DESCRIPTION OF EMBODIMENTS

Figure 1:
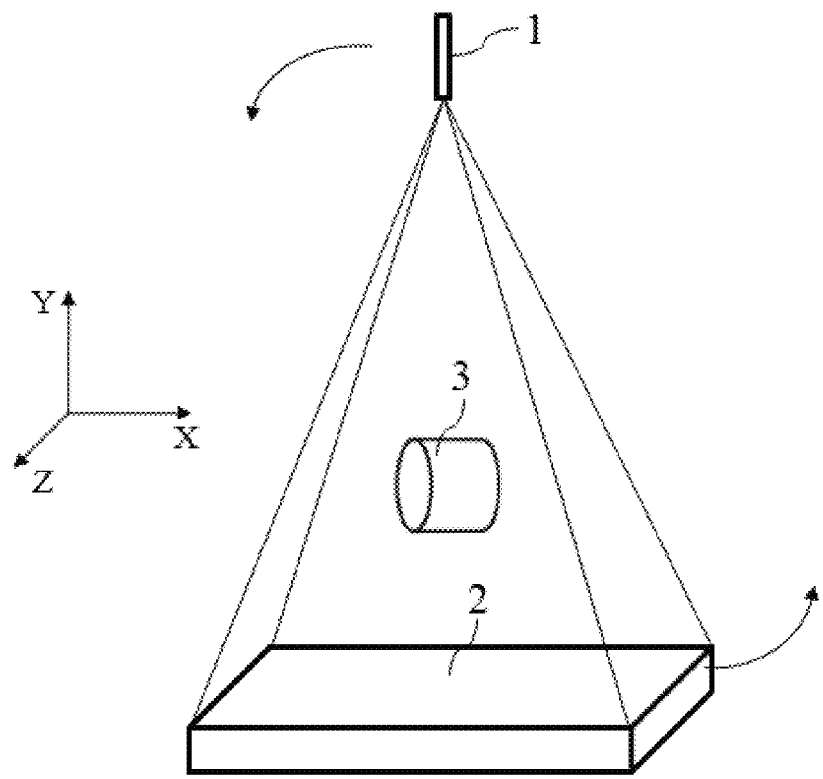
FIG. 1 is a schematic diagram showing the scanning principle of a CT in the prior art.

In the following, the invention will be described further with reference to embodiments. It should be understood that the following embodiments are for illustrative instead of limitative purpose only.

Notably, when a component or element is referred to as being "disposed on" another component or element, it can be directly disposed on the other component or element or there may be an intermediate component or element. When a component or element is referred to as being "connected or coupled" to another component or element, it may be directly connected or coupled to the other component or element or there is an intermediate component or element. The term "connection or coupling" used herein may include electrical connection or coupling and/or mechanical or physical connection or coupling. The term "comprise or include" used herein refers to the existence of features, steps, components or elements, but does not exclude the existence or addition of one or more further features, steps, components, or elements. The term "and/or" used herein includes any and all combinations of one or more of the related listed items.

Unless otherwise indicated, all the technical and scientific terms used herein have general meaning as commonly understood by those skilled in the technical field related to the disclosure. The terms used herein are for the purpose of describing specific embodiments, but not intended to limit the invention.

In addition, the terms "first", "second", "third" or the like used herein are only for the purpose of description and to distinguish similar objects from each other, which do not express the sequence thereof, nor can they be understood as an indication or implication of relative importance. In addition, in the description of this disclosure, unless otherwise specified, "a plurality of" means two or more.

In the invention, prior to processing the correction of the ring artifact in the CT image, it may first establish an additive noise model:

$$I(s,\theta)=I_r(s,\theta)+b(s)+\varepsilon(s,\theta) \quad \text{(Formula 1)}$$

wherein, I(s, θ) represents an actual detection value in a scanning angle θ and in a detector position s in the original sinogram by the CT scanning. The scanning angle θ and the detector position s may be customized depending on various application scenarios. Generally, it may select an initial irradiation direction of the X-ray generator as the reference direction for the scanning angle θ. The detector position s can be indicated according to the matrix arrangement of the detectors in the X-ray detector module. $I_r(s, \theta)$ represents an ideal detection value in the scanning angle θ and in the detector position s in an ideal sinogram; b(s) represents an offset value of an actual detection value of the detector channel corresponding to the detector position s, which offset value is irrespective of the angle, but is only related to whether the detector is damaged and to the effect of the output signal of the detector per se, and thus is the source of the ring artifact; ε(s, θ) represents a random error corresponding to the scanning angle θ and the detector position s in the original sinogram, and an expected value of the random error should be 0.

Figure 4:
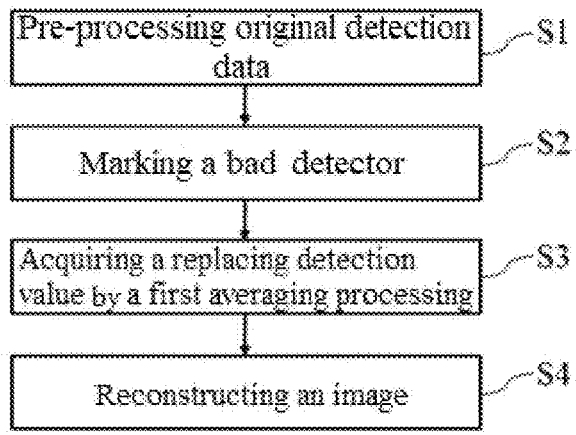
FIG. 4 is a schematic diagram of steps of a method of correction of a ring artifact in a CT image according to an embodiment of the invention.

FIG. 4 is a schematic diagram of steps of a method of correction of a ring artifact in a CT image according to an embodiment of the invention. As can be seen from FIG. 4, the method of correction of the ring artifact in the CT image provided in the invention may at least comprises the following steps:

step S1: pre-processing original detection data;
step S2: marking in detectors a bad detector based on the data in a pre-processed original sinogram;
Step S3: acquiring a replacing detection value corresponding to the bad detector by means of a first averaging processing; and
Step S4: performing a CT image reconstruction using a sinogram data after the first averaging processing.

Figure 5:
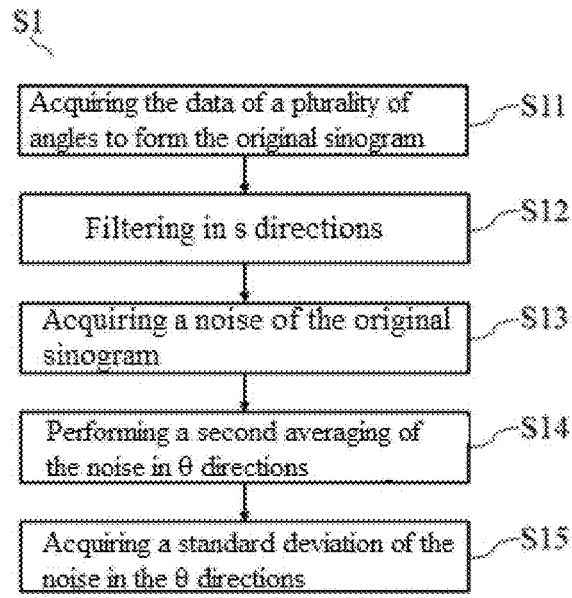
FIG. 5 is a schematic diagram of the step S1 of the method of correction of the ring artifact in the CT image according to an embodiment of the invention.

Specifically, as shown in FIG. 5, the above-mentioned step S1 further comprises the following steps of:
step S11: selecting actual detection values corresponding to a plurality of scanning angles θ from the original detection data to form the original sinogram;
step S12: filtering the original sinogram formed in the step S11 in directions of the detector positions s;
step S13: acquiring a noise of the original sinogram by means of the filtering;
step S14: performing a second average of the noise obtained in the step S13 in the θ directions; and
step S15: acquiring a standard deviation of the noise in the step S13 in the detector position s.

Figure 3:
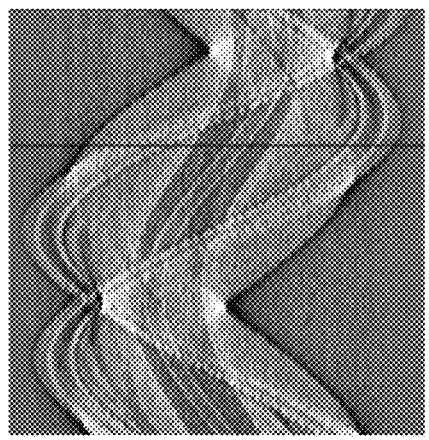
FIG. 3 is a schematic diagram of the sinogram acquired by carrying out a CT scanning in the prior art.

Specifically, in the step S11, the original sinogram is formed by selecting actual detection values corresponding to a plurality of scanning angles θ, that is I(s, θ). Generally, the number of scanning angles θ is not less than 50. In the original sinogram, the actual detection values may be intensities of the X-ray after attenuation, attenuation coefficients, or the attenuation coefficients after a slope filtering. It should be understood by the person skilled in the art that the slope filtering is a filtering method commonly used in the field. It may multiply by a slope function in the frequency domain space. The slope filtering comprises a standard slope filtering or a window slope filtering, and it may also use a convolution method to replace the slope filtering in the frequency domain space, which will not be elaborated herein. The attenuation coefficient is the ratio of the intensity of the attenuated X-ray detected by the detector to the intensity of the initial X-ray emitted by the X-ray. The sinogram formed in the step S11 is shown in FIG. 3, where the horizontal direction represents the detector positions s, and the vertical direction represents the scanning angles θ. For example, the black horizontal line in FIG. 3 represents actual detection values I(s, θ) of the detectors corresponding to a certain scanning angle θ in certain positions s.

Further, in the above-mentioned step S12, the filtering processing of the original sinogram in the s directions may be mean filtering, which may be performed according to the following formula:

$$I_r(s,\theta)=\Sigma_{-n}^{n}I(s+n,\theta)/(2n+1) \quad \text{(Formula 2)}$$

wherein, n is a natural number. That is, it may use the average value of the 2n+1 adjacent actual detection values I(s, θ) as the ideal detection value $I_r(s, \theta)$ of the corresponding position. For example, it may select the average value of three (n=1) actual detection values adjacent to a channel as the ideal detection value, in which case the above-mentioned Formula (2) will be:

$$I_r(s,\theta)=[I(s-1,\theta)+I(s,\theta)+I(s+1,\theta)]/3 \quad \text{(Formula 3)}$$

It should be understood by the person skilled in the art that the filtering process in step S12 may also be weighted filtering. The mean filtering is generally considered to be weighted filtering with equal weights, while the weighted filtering may also be Gaussian weighted filtering or other weighted filtering with high weights in the center and low weights on either side, which may be easily understood by the person skilled in the art according to the technical teaching of the invention in combination with mathematical knowledge, which will not be elaborated herein.

Figure 6:
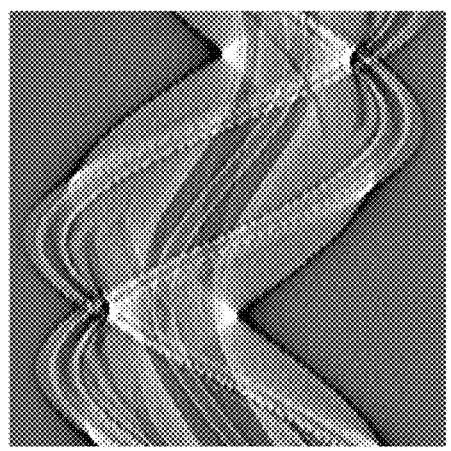
FIG. 6 is a schematic diagram of a corrected result by the method of correction of the ring artifact in the CT image of FIG. 5, in which the sinogram has been filtered.

The sinogram filtered through the above-mentioned step S12 may be regarded as an ideal sinogram, that is, the ideal sinogram formed by $I_r(s, \theta)$, as shown in FIG. 6. However, the filtered sinogram at this point cannot be directly used for CT image reconstruction, because this will lead to a great decrease in the spatial resolution of the CT image. It should be understood by the person skilled in the art that other filtering methods may also be used for processing in the step S12, which will not be listed herein. Meanwhile, the number n may also be selected according to actual needs or spatial resolution requirements, which will not be elaborated herein.

Figure 7:
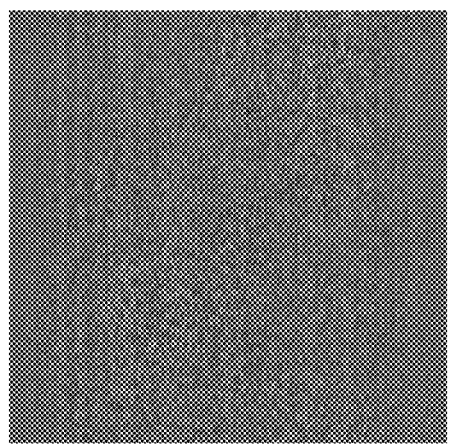
FIG. 7 is a schematic diagram of the noise by the method of correction of the ring artifact in the CT image according to FIG. 6.

In the above-mentioned step S13, the noise of the original sinogram is acquired by subtracting the ideal detection value data in the filtered ideal sinogram from the actual detection value data in the original sinogram, that is, by means of I(s, θ)−I$_r$(s, θ), the sum of the offset value outputted by the detector and the random error b(s)+ε(s, θ) is acquired, which is collectively referred to as the noise, as shown in FIG. 7.

In the above-mentioned step S14, the second averaging of the noise in the directions of the scanning angles θ may be specifically performed according to the following formula:

$$\hat{b}(s)=\Sigma_{\theta=1}^{N}[b(s)+\varepsilon(s,\theta)]/N=\Sigma_{\theta=1}^{N}[(I(s,\theta))-I_r(s,\theta)]/N \quad \text{(Formula 4)}$$

wherein, N is the number of the scanning angles θ selected in step S11, and $\hat{b}(s)$ represents an average offset value of all the offset values b(s) in all the scanning angle θ directions. According to the additive noise model established in the invention, since there is an ideal offset value b(s) as to the actual detection value I(s, θ) of each channel, in the application the ideal offset value b(s) may be replaced by the average offset value $\hat{b}(s)$ of all the ideal offset values b(s), that is, the average offset value $\hat{b}(s)$ can be made equal to the ideal offset value b(s) corresponding to each detection channel.

Figure 8:
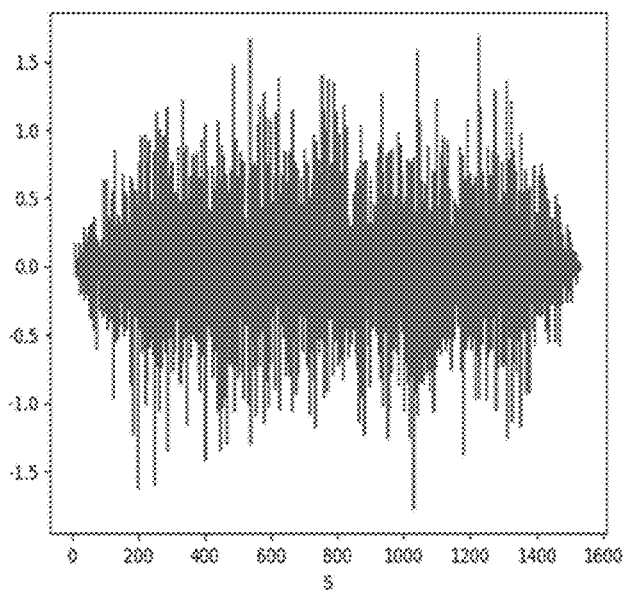
FIG. 8 is a schematic diagram of the offset by the method of correction of the ring artifact in the CT image according to FIG. 7.

For a detector channel, the mean value of the random errors ε(s, θ) thereof shall be 0, that is, when a detector position s is set, the mean value of random errors ε(s, θ) in the directions of the scanning angles θ shall be 0. By means of the second averaging, therefore, it may acquire the average offset values $\hat{b}(s)$ output by the detectors, as shown in FIG. 8, i.e., the average offset values $\hat{b}(s)$ corresponding to the detector positions s by means of the second averaging, wherein the abscissa represents the detector positions s, and the ordinate represents the average offset values $\hat{b}(s)$.

Figure 9:
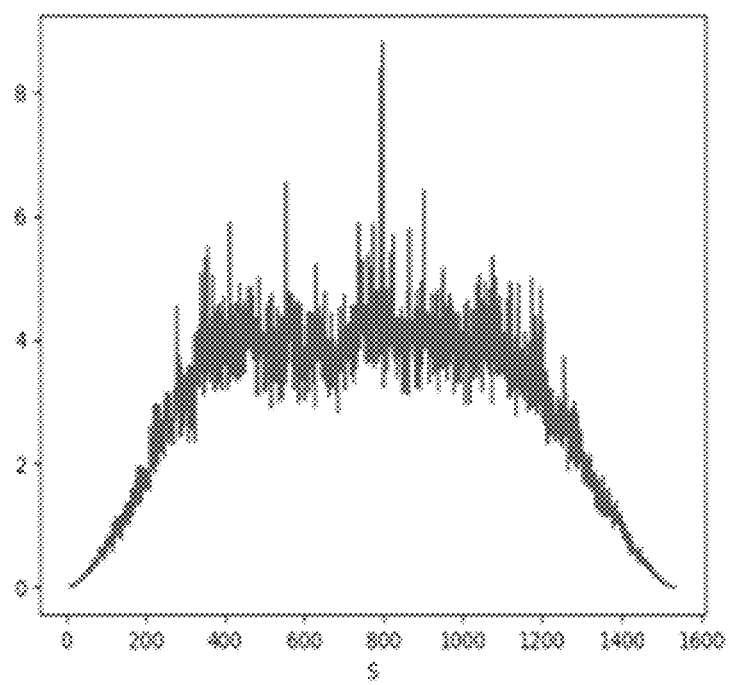
FIG. 9 is a schematic diagram of the offset standard deviation by the method of correction of the ring artifact in the CT image according to FIG. 7.

In the above-mentioned step S15, the standard deviation of the noise in the detector position s may be acquired according to the following formula:

$$\text{std}[\varepsilon(s)]=\Sigma_{\theta=1}^{N}[b(s)+\varepsilon(s,\theta)-\hat{b}(s)]^2/N \quad \text{(Formula 5)}$$

wherein, N is the number of scanning angles θ selected in the step S11, $\hat{b}(s)$ represents the average offset value of all the offset values b(s). Since the offset values b(s) outputted by the detector are constant in the θ directions, the standard deviation of the noise acquired in the detector position s will be the standard deviation std[ε(s)] of the random error ε(s, θ), which is essentially the random error in the detector position s, and is only related to the detector position s irrespective of the scanning angles θ, as shown in FIG. 9, in which the abscissa represents detection positions s, the ordinate represents the standard deviations std[ε(s)].

Figure 2:
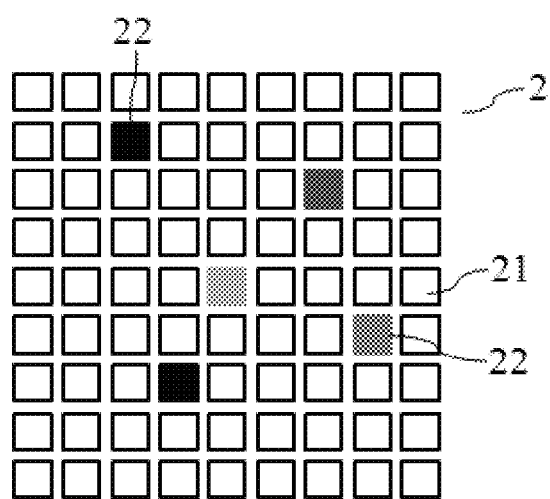
FIG. 2 is a schematic diagram of the X-ray detector module of the CT and the bad detectors in the X-ray detector module in the prior art.

In the above-mentioned step S2, marking the bad detector is performed by determining whether the following formula holds:

$$\text{abs}[\hat{b}(s)]>d\times\text{std}[\varepsilon(s)]\div\text{sqrt}(N) \quad \text{(Formula 6)}$$

wherein, abs[$\hat{b}(s)$] represents the absolute value of the average offset value $\hat{b}(s)$, d represents the correction coefficient, and sqrt(N) represents the root mean square of N. Since the offset value b(s) is the source of the ring artifact, the average offset value $\hat{b}(s)$ of excessiveness will lead to the ring artifact, such that it is needed to determine which channel has an excessive average offset value $\hat{b}(s)$. For each detector position s, it is determined whether the average offset value $\hat{b}(s)$ is of excessiveness according to whether Formula (6) holds. If the Formula (6) holds, it is determined that the average offset value $\hat{b}(s)$ is of excessiveness, and thus the channel corresponding to the detector position s is marked as a bad detector. The marked bad detectors are shown in FIG. 2, in which all the blocks with different gray values represent the bad detectors.

A theoretical basis of the determination method is hypothesis testing. Although the distribution pattern of the offset values b(s) is unknown, it can be known from the central limit theorem that the average offset values $\hat{b}(s)$ satisfy a Gaussian distribution. For normal detectors, their offset values b(s) shall be 0, that is, the mean value of the calculated average offset values $\hat{b}(s)$ is 0. Due to the existence of errors, the average offset values $\hat{b}(s)$ actually satisfy a Gaussian distribution with a mean value of 0 and a standard deviation of std[ε(s)]÷sqrt(N). In the Gaussian distribution, the probability of abs[b(s)]<d×std[ε(s)]÷sqrt(N) is relatively great, for example, when d=1.96, the probability of abs[b(s)]<d×std[ε(s)]÷sqrt(N) is 95%. Therefore, the probability of satisfying the Formula (6) is only 5%, which is a very small probability. It is typically considered there is a reason for the occurrence of a small probability event, that is, the offset value b(s) is not 0, indicating that there is a bad detector in a certain position s of the detectors.

Further, in the above-mentioned Formula (6), the correction coefficient d corresponds to a probability used to determine whether there is a small probability event. For example, when d=1.96, the corresponding probability that the above-mentioned Formula (6) holds is only 5%. In such a case, 5% is considered a small probability event. Generally, the correction coefficient is in a range of 1.6-2.6. When the correction coefficient d is in a range of 1.6-1.8, almost all ring artifacts may be eliminated by the correction method proposed in the invention, but the spatial resolution will be slightly reduced. When the correction coefficient d is in a range of 1.8-2.0 (preferably 1.96), almost all ring artifacts may be eliminated by the correction method proposed in the invention, while the spatial resolution is barely not affected. When the correction coefficient d is in a range of 2.0-2.6, most of the ring artifacts may be eliminated by the correction method proposed in the invention, while the spatial resolution is hardly affected.

Figure 10:
FIG. 10 is a schematic diagram of the averaging in the method of correction of the ring artifact in the CT image according to an embodiment of the invention.

In an embodiment of the invention, in the above-mentioned step S3, after acquiring the bad detector information, acquiring the replacing detection value of the detector that results in the bad channel by means of the first averaging processing comprises a specific method as follows:

For a one-dimensional channel arrangement of the CT detectors, as shown in FIG. 10, the actual detection values of the detectors corresponding to the 2n channels adjacent to the bad detector in the s directions are averaged as the replacing detection value corresponding to the bad detector. For example, in FIG. 10, when there are 9 detectors in a one-dimensional arrangement and one detector in the middle is a bad detector, the actual detection values of all the other eight detectors in the row except the bad detector may be averaged as the replacing detection value of the bad detector. That is, n is 4, and on each side of the bad detector, the respective four detectors' actual detection values are taken. Alternatively, the actual detection values of the other four detectors on the left and right sides of the bad detector in the row except the bad detector may be averaged as the replacing detection value of the bad detector. That is, n is 2, and on each side of the bad detector, the respective two detectors' actual detection values are taken. It should be understood by the person skilled in the art that, the averaging method as shown in FIG. 10 is also applicable for two-dimensional channels.

Figure 11:
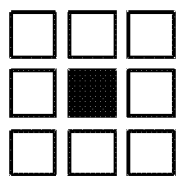
FIG. 11 is a schematic diagram of one kind of the averaging in the method of correction of the ring artifact in the CT image according to an embodiment of the invention.
Figure 12:
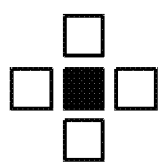
FIG. 12 is a schematic diagram of one kind of the averaging in the method of correction of the ring artifact in the CT image according to an embodiment of the invention.
Figure 13:
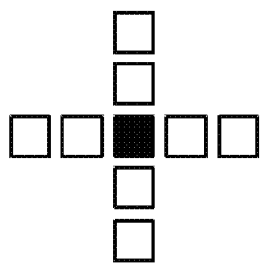
FIG. 13 is a schematic diagram of one kind of the averaging in the method of correction of the ring artifact in the CT image according to an embodiment of the invention.
Figure 14:
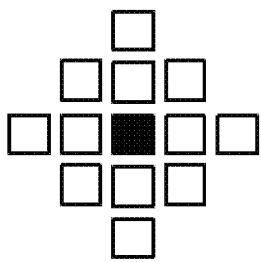
FIG. 14 is a schematic diagram of one kind of the averaging in the method of correction of the ring artifact in the CT image according to an embodiment of the invention.

For a two-dimensional channel arrangement, the actual detection values of the detectors corresponding to the channels next to or adjacent to the bad detector are averaged as the replacing detection value corresponding to the bad detector. It should be understood by the person skilled in the art that "next to" in this application means a detector immediately adjacent to the detector resulting in the bad channel, that is, there is no other detector between the detector resulting in the bad channel and the next-to detector; while "close" or "adjacent" means detectors near to the detector resulting in the bad channel, that is, there may be other detectors between the detector resulting in the bad channel and the close or adjacent detector. For example, in FIG. 11, the actual detection values of eight detectors surrounding the bad detector may be averaged as the replacing detection value of the bad detector. In FIG. 12, the actual detection values of the four detectors adjacent to the bad detector on the up, down, left and right sides may be averaged as the replacing detection value of the bad detector. In FIG. 13, the actual detection values of eight detectors in orthogonal directions to the bad detector may be averaged as the replacing detection value of the bad detector. In FIG. 14, the actual detection values of twelve detectors adjacent to the bad detector may be averaged as the replacing detection value of the bad detector.

In a further embodiment of the invention, in the above-mentioned step S3, prior to performing the first averaging processing, it may use an approximate value $I(s, \theta)-\bar{b}(s)$ acquired by subtracting the average offset value from the actual detection value of each detector as the basis of the first averaging processing. For example, where the CT detectors are arranged in a one-dimensional arrangement, the first averaging processing may use the average value of the approximate values of the 2n detectors adjacent to the bad detector on both sides thereof as the replacing detection value of the bad detector. It should be understood by the person skilled in the art that, for performing the first averaging processing, it may use the weighted actual detection values as the basis of the first averaging processing, which will not be elaborated herein.

In the above-mentioned step S4, the CT image reconstruction using the data processed by the first averaging may correspond to the method of image reconstruction in the prior art, which will not be elaborated herein.

Figure 15:
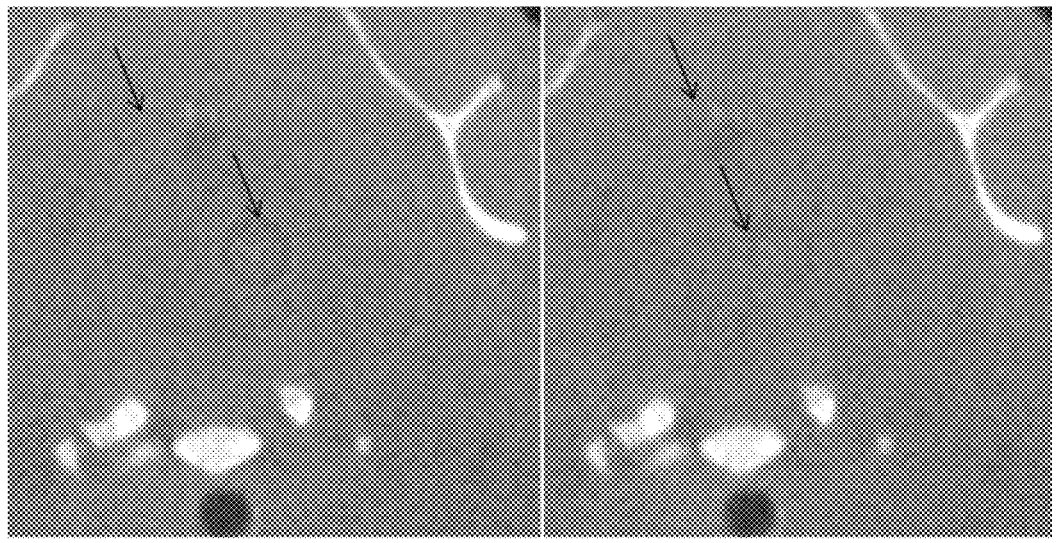
FIG. 15 is a schematic diagram of the correction effect by the method of correction of the ring artifact in the CT image according to an embodiment of the invention.

FIG. 15 is a schematic diagram of the correction effect by the method of correction of the ring artifact in the CT image according to an embodiment of the invention. In FIG. 15, the portions indicated by the arrows in the left figure show the ring artifacts, while the arrows in the right figure indicate the corresponding regions of the CT image after eliminating the ring artifacts. Apparently, the ring artifacts have been almost completely eliminated by the invention and the spatial resolution of the CT image is hardly affected.

Figure 16:
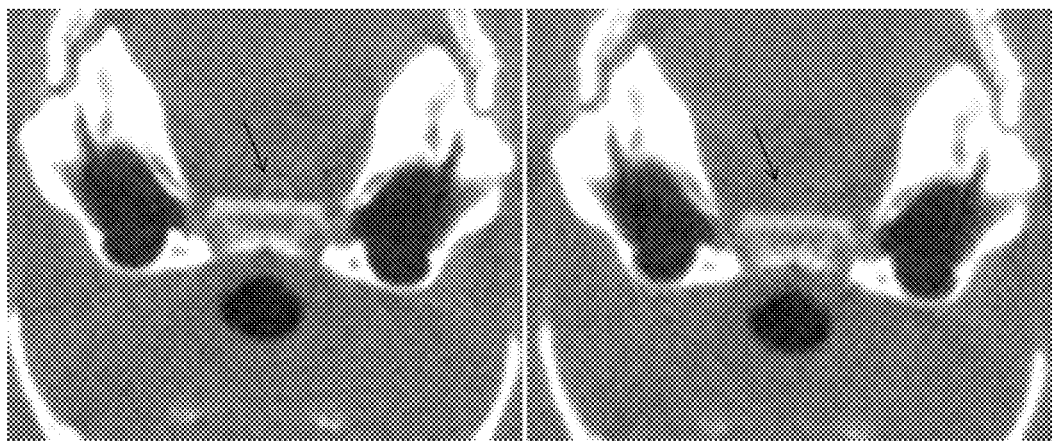
FIG. 16 is a schematic diagram of the correction effect by the method of correction of the ring artifact in the CT image according to an embodiment of the invention.

FIG. 16 is a schematic diagram of the correction effect by the method of correction of the ring artifact in the CT image according to an embodiment of the invention. In FIG. 16, the portions indicated by the arrow in the left figure show the ring artifact, while the arrow in the right figure indicate the corresponding regions of the CT image after eliminating the ring artifacts. Apparently, the ring artifacts have been almost completely eliminated by the invention and the spatial resolution of the CT image is hardly affected.

In the invention, the obvious ring artifact in the image is usually generated by the bad channel, such that by analyzing the additive noise model, it may effectively detect the obvious bad channel using the method based on the hypothesis test in the statistical principle, and it may also eliminate the obvious ring artifact in the image by replacing the detection value of the bad detector with the average value of the detection values of the adjacent detectors. The ring artifact which is not particularly obvious in the image is usually caused by the inconsistency of the channel detection efficiency. The invention represents the effect of suppressing the ring artifact by subtracting the offset value of the channel to determine its detection efficiency. The invention only needs to replace the bad detector, which is in a small proportion, with the average value of the adjacent channels, so as to reduce the loss of the spatial resolution of the image to the greatest extent and ensure the quality of the image.

Figure 17:
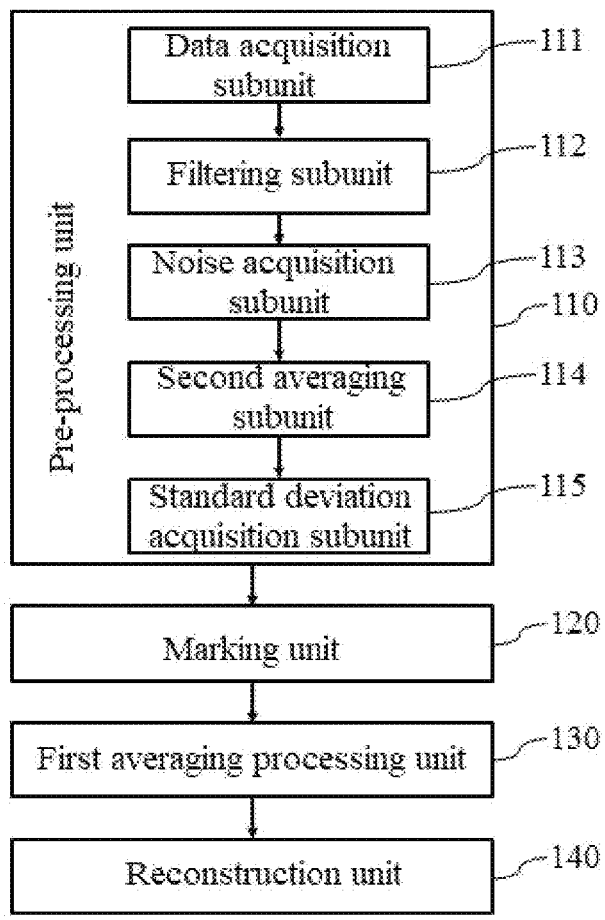
FIG. 17 is a schematic diagram of an arrangement of a device of correction of a ring artifact in a CT image according to an embodiment of the invention.

In the embodiment of the application provided is a device of correction of a ring artifact in a CT image. As shown in FIG. 17, the correction device at least comprises:

a pre-processing unit 110 which may be configured to pre-process original detection data, and may output offset values of actual detection values of detectors in various positions;

a marking unit 120 which may be configured to mark a bad detector of the detectors according to data in the pre-processed original sinogram;

a first averaging processing unit 130 which may be configured to acquire a replacing detection value corresponding to the bad detector by means of a first averaging processing, or configured to subtract each offset value from the actual detection value of each detector prior to the first averaging processing; and a reconstruction unit 140 which may be configured to perform a CT image reconstruction using a sinogram data after the first averaging processing.

Furthermore, the above-mentioned pre-processing unit may comprise:

a data acquisition subunit 111 which may be configured to select actual detection values corresponding to a plurality of scanning angles from the original detection data to form the original sinogram;

a filtering subunit 112 which may be configured to filter the original sinogram in directions of detector positions s;

a noise acquisition subunit 113 which may be configured to acquire a noise of the original sinogram by means of the filtering;

a second averaging subunit 114 which may be configured to perform a second average of the noise in directions of the scanning angles $\theta$ and may output the offset values of the actual detection values of the detectors in the various positions; and a standard deviation acquisition subunit 115 which may be configured to acquire a standard deviation of the noise in the directions of the scanning angles $\theta$.

The details of the respective units and subunits may make reference to the description of steps S1 to S4 and steps S11 to S15 in the foregoing method embodiments, which will not be elaborated herein.

The correction device may be a server, an electronic device, etc., or any device capable of performing data processing based on a sinogram, which is not limited herein. It should be noted that the functions implemented by the units in the above-mentioned correction devices may also be implemented by executing instructions stored in a memory by a processor in a computer.

In the invention, provided is a computer storage medium in which program instructions are stored, and when executed, realize the following functions: pre-processing an original sinogram, and outputting offset values of actual detection values of detectors in various positions; marking a bad detector in the pre-processed original sinogram; acquiring a replacing detection value corresponding to the bad detector by means of a first averaging processing, or subtracting each offset value from the actual detection value of each detector, and then acquiring a replacing detection value corresponding to the bad detector by means of the first averaging processing; and performing a CT image reconstruction using the data after the first averaging processing.

The above-mentioned program instructions may be executed by a processor or may be executed by other processing devices.

It should be understood by the person skilled in the art that all or part of the steps in the above-mentioned method embodiments may be implemented by instructing relevant hardware through computer programs, which may be stored in a non-volatile computer-readable storage medium, and when executed, may include the processes of the method in above-mentioned embodiments. Among others, any reference to memory, storage medium, database or other medium used in the various embodiments of the invention may include non-volatile and/or volatile memory. The non-volatile memory may comprise Read-Only Memory (ROM), Programmable ROM (PROM), Electrically Programmable ROM (EPROM), Electrically Erasable Programmable ROM (EEPROM), or flash memory. The volatile memory may comprise random access memory (RAM) or external cache memory. As a demonstration but not a limitation, RAM may be in various forms, such as Static RAM (SRAM), Dynamic RAM (DRAM), Synchronous DRAM (SDRAM), Double Data Rate SDRAM (DDRSDRAM), Enhanced SDRAM (ESDRAM), Synchronous Link (Synchlink) DRAM (SLDRAM), RAM Bus (Rambus) Direct RAM (RDRAM), Direct RAM Bus Dynamic RAM (DRDRAM), and RAM Bus Dynamic RAM (RDRAM) or the like.

The devices, units, subunits, or the like described in the above embodiments may be specifically implemented by computer chips and/or components or implemented by products with specific functions. For the convenient purpose, the description of the devices is made respectively of individual units by functions. Of course, when implementing the disclosure, the functions of the individual units may be embodied in the same or various computer chips.

What have been described above are only preferred embodiments of the invention and are not intended to limit the scope of the invention. Various alternatives may be made to the said embodiments of the invention. In this regard, any simple or equivalent change or modification made according to the claims and the description falls within the scope of the invention as prescribed in the claims. What is not described in detail in the disclosure is conventional.

What is claimed is:

1. A method of correction of a ring artifact in a CT image, wherein the method of correction comprises:
    pre-processing original detection data, comprising:
        selecting actual detection values corresponding to a plurality of scanning angles θ from the original detection data to form an original sinogram;
        filtering the original sinogram in directions of detect positions s;
        acquiring a noise of the original sinogram by means of the filtering;
        performing a second averaging of the noise in directions of the scanning angles θ; and
        acquiring a standard deviation of the noise of the original sinogram in the θ directions;
    marking in detectors a bad detector based on data in a pre-processed original sinogram;
    acquiring a replacing detection value corresponding to the bad detector by means of a first averaging processing; and
    performing a CT image reconstruction using a sinogram data after the first averaging processing.

2. The method of correction of the ring artifact in the CT image of claim 1, wherein the method of correction further comprises establishing an additive noise model prior to the pre-processing:

$I(s,\theta)=I_r(s,\theta)+b(s)+\varepsilon(s,\theta)$, wherein, $I(s, \theta)$ represents an actual detection value in a scanning angle θ and in a detector position s in the original sinogram, and $I_r(s, \theta)$ represents an ideal detection value in the scanning angle θ and in the detector position s in an ideal sinogram; $b(s)$ represents an offset value of the actual detection value corresponding to the detector position s, and $\varepsilon(s, \theta)$ represents a random error corresponding to the scanning angle θ and the detector position s in the original sinogram.

3. The method of correction of the ring artifact in the CT image of claim 1, wherein the number of the selected scanning angles θ is not less than 50.

4. The method of correction of the ring artifact in the CT image of claim 1, wherein the actual detection values are intensities of the X-ray after attenuation measured by the detector, attenuation coefficients, or the attenuation coefficients after a slope filtering.

5. The method of correction of the ring artifact in the CT image of claim 1, wherein the filtering is weighted filtering.

6. The method of correction of the ring artifact in the CT image of claim 5, wherein the weighted filtering is mean filtering which employs the following formula:

$I_r(s,\theta)=\Sum_{-n}^{n}I(s+n,\theta)/(2n+1)$, where n is a natural number.

7. The method of correction of the ring artifact in the CT image of claim 1, wherein the noise is acquired by subtracting ideal detection values in an ideal sinogram after the filtering from the actual detection values in the original sinogram.

8. The method of correction of the ring artifact in the CT image of claim 7, wherein the second averaging of the noise in the directions of the scanning angles θ may be specifically performed according to the following formula:

$\hat{b}(s)=\Sum_{\theta=1}^{N}[b(s)+\varepsilon(s,\theta)]/N$, wherein, $\hat{b}(s)$ represents an average offset value of offset values $b(s)$ in the directions of all the scanning angles θ, and N is the number of the scanning angles θ selected.

9. The method of correction of a ring artifact in a CT image of claim 8, wherein the standard deviation of the noise in the detector position s is acquired according to the following formula:

$std[\varepsilon(s)]=\Sum_{\theta=1}^{N}[b(s)+\varepsilon(s,\theta)-\hat{b}(s)]^2/N$, wherein N is the number of the scanning angles θ selected.

10. The method of correction of the ring artifact in the CT image of claim 9, wherein marking the bad detector is performed by determining whether the following formula holds:

$abs[\hat{b}(s)]>d\times std[\varepsilon(s)]\div sqrt(N)$  (Formula 6)

wherein, $abs[\hat{b}(s)]$ represents an absolute value of the average offset value $\hat{b}(s)$, d represents a correction coefficient, sqrt(N) represents a root mean square of N, and if the Formula (6) holds, it is determined that the average offset value b̂(s) is of excessiveness, and the corresponding channel is marked as the bad detector.

11. The method of correction of the ring artifact in the CT image of claim 10, wherein the correction coefficient d is in a range of 1.6-2.6, 1.8-2.0 or 2.0-2.6.

12. The method of correction of the ring artifact in the CT image of claim 10, wherein the correction coefficient d is 1.96.

13. The method of correction of the ring artifact in the CT image of claim 1, wherein the first averaging processing comprises a specific step of: using an average value of actual detection values of the 2n detectors adjacent to the bad detector on both sides thereof in the same line as the replacing detection value of the bad detector, wherein n is a natural number.

14. The method of correction of the ring artifact in the CT image of claim 1, wherein where the CT detectors are arranged in a two-dimensional arrangement, the first averaging processing comprises a specific step of: using an average value of actual detection values of the four detectors next to the bad detector as the replacing detection value of the bad detector.

15. The method of correction of the ring artifact in the CT image of claim 1, wherein where the CT detectors are arranged in a two-dimensional arrangement, the first averaging processing comprises using an average value of actual detection values of the eight detectors adjacent to the bad detector as the replacing detection value of the bad detector.

16. The method of correction of the ring artifact in the CT image of claim 1, wherein where the CT detectors are arranged in a two-dimensional arrangement, the first averaging processing comprises a specific step of: using an average value of actual detection values of the eight detectors in orthogonal directions to the bad detector as the replacing detection value of the bad detector.

17. The method of correction of the ring artifact in the CT image of claim 1, wherein where the CT detectors are arranged in a two-dimensional arrangement, the first averaging processing comprises a specific step of: using an average value of actual detection values of the twelve detectors adjacent to the bad detector as the replacing detection value of the bad detector.

18. The method of correction of the ring artifact in the CT image of claim 13, wherein in the first averaging processing, the actual detection value of each detector is replaced by subtracting a corresponding average offset value from the actual detection value thereof.

19. The method of correction of the ring artifact in the CT image of claim 1, wherein in the sinogram data, only the data at the bad detector is replaced by the replacing detection value, and the sinogram data at non-bad detectors remain the same as the original sinogram.

20. The method of correction of the ring artifact in the CT image of claim 9, wherein in the sinogram data, only the data at the bad detector is replaced by the replacing detection value, and the sinogram data at non-bad detectors are replaced by subtracting the average offset value from the original sinogram.

21. A device of correction of a ring artifact in a CT image, wherein the device of correction comprises:
 a pre-processing unit configured to pre-process original detection data, comprising:
  data acquisition subunit configured to select actual detection values corresponding to a plurality of scanning angles from the original detection data to form an original sinogram;
  a filtering subunit configured to filter the original sinogram in directions of the detector positions s;
  a poise acquisition subunit configured to acquire a noise of the original sinogram by means of the filtering;
  a second averaging subunit configured to perform a second averaging of the noise in directions of the scanning angles; and
  a standard deviation acquisition subunit configured to acquire a standard deviation of the noise in the directions of the scanning angles;
 a marking unit configured to mark a bad detector according to the data in the pre-processed original sinogram;
 a first averaging processing unit configured to acquire a replacing detection value corresponding to the bad detector by means of a first averaging processing; and
 a reconstruction unit configured to perform a CT image reconstruction using a sinogram data after the first averaging processing.

22. The device of correction of the ring artifact in the CT image of claim 21, wherein the second averaging subunit is configured to output an offset value of the actual detection value after the second average.

23. The device of correction of the ring artifact in the CT image of claim 21, wherein the first averaging processing uses an average value of the actual detection values of the 2n detectors adjacent to the bad detector on both sides thereof in the same line as the replacing detection value of the bad detector, n is a natural number.

24. The device of correction of the ring artifact in the CT image of claim 21, wherein where the CT detectors are arranged in a two-dimensional arrangement, the first averaging processing uses an average value of the actual detection values of the four detectors next to the bad detector as the replacing detection value of the bad detector.

25. The device of correction of the ring artifact in the CT image of claim 21, wherein where the CT detectors are arranged in a two-dimensional arrangement, the first averaging processing uses an average value of the actual detection values of the eight detectors adjacent to the bad detector as the replacing detection value of the bad detector.

26. A non-transitory computer storage medium, wherein in the computer storage medium, program instructions are stored, and when executed, achieve the following functions:
 pre-processing an original sinogram, comprising:
  selecting actual detection values corresponding to a plurality of scanning angles θ from the original detection data to form an original sinogram;
  filtering the original sinogram in directions of detect positions s;
  acquiring a noise of the original sinogram by means of the filtering;
  performing a second averaging of the noise in directions of the scanning angles θ; and
  acquiring a standard deviation of the noise of the original sinogram in the θ directions;
 marking a bad detector in the pre-processed original sinogram;
 acquiring a replacing detection value corresponding to the bad detector by means of a first averaging processing; and
 performing a CT image reconstruction using data after the first averaging processing.

27. The method of correction of the ring artifact in the CT image of claim 14, wherein in the first averaging processing, the actual detection value of each detector is replaced by subtracting a corresponding average offset value from the actual detection value thereof.

28. The method of correction of the ring artifact in the CT image of claim 15, wherein in the first averaging processing, the actual detection value of each detector is replaced by subtracting a corresponding average offset value from the actual detection value thereof.

29. The method of correction of the ring artifact in the CT image of claim 16, wherein in the first averaging processing, the actual detection value of each detector is replaced by subtracting a corresponding average offset value from the actual detection value thereof.

30. The method of correction of the ring artifact in the CT image of claim 17, wherein in the first averaging processing, the actual detection value of each detector is replaced by subtracting a corresponding average offset value from the actual detection value thereof.

* * * * *